United States Patent
Knight et al.

(10) Patent No.: US 8,328,881 B2
(45) Date of Patent: Dec. 11, 2012

(54) HAIR TREATMENT COMPOSITION

(75) Inventors: Penelope Eileen Knight, Bedford (GB); Richard Awerkwei Quartey, Milton Keynes (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/389,986

(22) PCT Filed: Aug. 17, 2010

(86) PCT No.: PCT/EP2010/061978
§ 371 (c)(1),
(2), (4) Date: Feb. 10, 2012

(87) PCT Pub. No.: WO2011/020833
PCT Pub. Date: Feb. 24, 2011

(65) Prior Publication Data
US 2012/0138079 A1    Jun. 7, 2012

(30) Foreign Application Priority Data
Aug. 21, 2009 (EP) .................................. 09168375

(51) Int. Cl.
*A61Q 5/10* (2006.01)

(52) U.S. Cl. ............ 8/405; 8/425; 8/435; 8/452; 8/460; 8/646

(58) Field of Classification Search .............. 8/405, 425, 8/435, 452, 460, 646
See application file for complete search history.

(56) References Cited

U.S. PATENT DOCUMENTS

| 7,186,279 B2 * | 3/2007 | Palpu et al. ................... 8/405 |
| 2006/0143838 A1 | 7/2006 | Palpu et al. |
| 2007/0116652 A1 | 5/2007 | Kamath et al. |

FOREIGN PATENT DOCUMENTS

| EP | 345571 | 5/1989 |
| EP | 345571 A1 | 5/1989 |
| FR | 2730408 | 8/1996 |
| FR | 2730408 A1 | 8/1996 |
| WO | WO2006061847 A1 | 6/2006 |

OTHER PUBLICATIONS

PCT International Search Report on Application No. PCT/EP2010061978, dated Nov. 5, 2010.
Written Opinion on Application No. PCT/EP20100601978, dated Nov. 5, 2010.
European Search Report EP 09 168375, Dated Mar. 2, 2010.

* cited by examiner

*Primary Examiner* — Eisa Elhilo
(74) *Attorney, Agent, or Firm* — Ronald A. Koatz

(57) ABSTRACT

This invention relates to a permanent dye for coloring keratinous fibers comprising: (a) A solution of iron (II) or iron (III) salt; (b) A solution of an aqueous extract of *Terminalia chebula* and (c) A solution of at least one color developer selected from the group consisting of a polyphenol and polyphenol derivatives or mixture thereof. A method of coloring keratinous fibers using the permanent dye is also provided.

10 Claims, No Drawings

HAIR TREATMENT COMPOSITION

This invention relates to a permanent dye for colouring keratinous fibres, in particular one based on the extract of *Terminalia chebula*, also known as Black Myrobalan or Chebulic Myrobalan, a 30 meters tall evergreen tree native to southern Asia from India/Nepal to southwestern China to Sri Lanka, Malaysia and Vietnam bearing 2 to 4.5 cm long dark drupe-like fruit with longitudinal ridges.

Non-permanent hair colour comprises either active species which are larger than 10 Angstroms and can only coat the hair shaft rather than diffuse through the pores into the hair shaft or active species which are no larger than 10 Angstroms and can diffuse through the pores into the hair shaft but can equally diffuse out. Permanent hair colour comprises active species which are no larger than 10 Angstroms and can diffuse through the pores into the hair shaft but once within the hair shaft are able to react or associate with either another species to form a product larger than 10 Angstroms or the internal surface of the hair shaft and thereby to become trapped within the hair shaft.

This invention provides a permanent dye for colouring keratinous fibres based on a naturally derived product.

SUMMARY OF THE INVENTION

In a first aspect of the invention, a permanent dye for colouring keratinous fibres is provided, the permanent dye comprising:
(a) A solution of iron (II) or iron (III) salt;
(b) A solution of an aqueous extract of *Terminalia chebula*; and
(c) A solution of at least one colour developer selected from the group consisting of a polyphenol, the breakdown products of a polyphenol, derivatives thereof and mixtures of polyphenols;
wherein the iron (II) or iron (III) salt and the at least one colour developer selected from the group consisting of a polyphenol, the breakdown products of a polyphenol and derivatives thereof react to form a complex, and
wherein the polyphenol, the breakdown products of a polyphenol, derivatives thereof and mixtures of polyphenols is not in the form of an aqueous extract of *terminalia chebula*.

It is believed that at least some of the components of the aqueous extract of *Terminalia chebula* also react with the iron (II) or iron (III) salt to form a complex. Thus if solution (a) is applied to the hair shaft and allowed to diffuse into the hair shaft first followed by treatment of the hair shaft with solution (b) or (c), a complex forms within the hair shaft between the at least some of the components of the aqueous extract of *Terminalia chebula*, the polyphenol, the breakdown products of the polyphenol and derivatives thereof, which also diffuse into the hair shaft, and the already present iron (II) or iron (III) salt thereby to form a complex too large to diffuse out of the hair shaft thus resulting in permanent colouring of the hair shaft. Of course, the sequence of treatment with the solutions may be reversed so that solutions (b) and (c) are applied to the hair shaft first followed by treatment of the hair shaft with solution (a).

The polyphenol may be selected from the group consisting of epigallocatechin; epigallocatechin gallate; methyl gallate; gallic acid; one or more provided by an aqueous extract of green tea, preferably by an aqueous extract of green tea comprising more than 80% by weight polyphenols, more than 80% by weight catechins and less than 1% by weight caffeine; and mixtures thereof.

By the term "catechins" is meant any catechin(s) selected from the group consisting of catechin, gallocatechin, catechin gallate, gallocatechin gallate, epicatchin, epigallocatechin, epigallocatechin gallate, epigallocatechin gallate and mixtures thereof.

The pH of solutions (a) and (b) is preferably in the range 1 to 7, preferably 3 to 7, most preferably 6 to 7 as this pH is more compatible with skin and the hair.

In one embodiment, the iron salt is an iron (II) salt.

In a second aspect of the invention, a method of colouring keratinous fibres using the permanent dye of the first aspect is provided, the method comprising the steps of:
(a) Mixing solutions (b) and (c) thereby to produce solution (d);
(b) Applying solution (a) to hair; and
(c) Applying solution (d) to hair,
wherein steps (a) and (b) may be carried out in either order.

Preferably step (b) precedes step (c).

The method preferably comprises the additional step of rinsing the hair with water between steps (b) and (c). It is believed that this prevents formation of a complex on the exterior surface of a hair shaft which may partially block diffusion of solutions (a) or (d) into the hair shaft resulting in a lower level of permanent hair colouring.

Preferably one or both of step (b) or step (c) is carried out at room temperature. It has been observed that best results are obtained when hair is treated at room temperature. One advantage is that the inventive method is less harsh on the hair than one requiring the application of heat.

DETAILED DESCRIPTION OF THE INVENTION

Materials

Amigel (a homopolymer of glucose with a molecular weight of 5-6 M Daltons obtained by fermentation of *Sclerotium rolfsii* in the presence of a glucose-enriched medium) was purchased from Alban Muller International, the thickener Sylvaclear WF1500 was obtained from Arizona Chemicals (USA), Glydant Plus (a mixture of 1,3-dimethyloyl-5,5-dimethylhydantoin and 3-iodo-2-propynyl butyl carbamate) was obtained from Lonza, Carbopol ETD2020 (acrylates/$C_{10-30}$ alkyl acrylate crosspolymer) was obtained from Lubrizol, caffeine obtained from Sigma-Aldrich Company and the aqueous extract of *Terminalia chebula* was obtained from Siris Impex (Sirinagar, Vijayawada, Andhra Pradesh, INDIA, 520 007). A range of green teas, namely Sunphenon 40R (which comprises more than 40% polyphenols, more than 30% catechins and less than 10% caffeine), Sunphenon 90M (which comprises more than 80% polyphenols, more than 75% catechins and less than 6% caffeine) and Sunphenon 90LB (which comprises more than 80% polyphenols, more than 80% catechins but with less than 1% caffeine) were obtained from Taiyo Kagaku Company Limited. The real human hair swatches (NW 10/2 G RND (Natural White 2 grams/10 inches net round)) were purchased from International Hair Importers & Products Incorporated (Glendale, N.Y., USA, 11385).

Hair Colour Scale

The following subjective measurement scale was used:

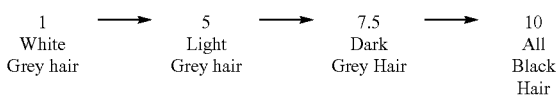

Formulations
Component Activator Gel Formulation (Weight):

| Component A | $FeCl_2 \cdot 4H_2O$ | 11.80 |
| --- | --- | --- |
| | Sodium dithionate | 1.20 |
| | Amigel | 1.50 |
| | Hydrochloric acid | pH~1.5 |
| | Water | 93.54 |
| Component B | Propylene carbonate | 60.00 |
| | Propylene glycol | 40.00 |
| Component C | Propionic acid | 7.45 |
| | Potassium hydroxide | 2.80 |
| | Water | 97.20 |

The component activator gel was prepared at room temperature by combining component A, B and C in the weight ratio of components 5:2:3 respectively.

Component Developer Gel Formulation (Weight):

| Component A | Methyl gallate | 0.10 |
| --- | --- | --- |
| | Water | 100.00 |
| Component B | Carbopol ETD2020 | 0.60 |
| | Sodium sulphite | 0.38 |
| | Water | 100.00 |
| Component C | *Terminalia chebula* extract | 10.00 |
| | Water | 100.00 |

Component C was prepared by heating the solution at 60 degrees centigrade for 45 minutes and then centrifuging the solution at high speed. The component developer gel was prepared by combining components A, B and C at room temperature in the weight ratio of 3.3:13.3:33.3.

All-in-One Activator Gel Formulation (% Weight):

| $FeCl_2 \cdot 4H_2O$ | 3.76 |
| --- | --- |
| Sodium dithionate | 0.63 |
| Amigel | 1.30 |
| Glydant Plus | 0.05 |
| Water | 71.26 |
| Propylene carbonate | 12.00 |
| Propylene glycol | 8.00 |
| Propionic acid | 1.12 |
| Potassium propionate | 1.68 |
| Sylvaclear WF 1500 | 0.20 |
| pH 4-4.5. | |

The all-in-one activator gel was prepared at room temperature by adding all the ingredients into a reactor vessel and mixing.

All-in-One Developer Gel Formulation (% Weight):

| Methyl gallate | 1.00 |
| --- | --- |
| Glydant Plus | 0.15 |
| Carbopol ETD2020 | 0.80 |
| Sodium sulphite | 0.38 |
| Ethylenediamine tetraacetate | 0.05 |
| *Terminalia chebula* extract | 1.00 |
| Sodium hydroxide | 0.48 |
| Water | 96.14 |
| pH 7-8. | |

The all-in-one developer gel was prepared at room temperature by adding all the ingredients into a reactor vessel and mixing.

Examples 1 to 5

Example 1: The component activator gel only was applied to hair swatches.
Example 2: The component developer gel only was applied to hair swatches
Example 3: The all-in-one activator gel and the all-in-one developer gel were applied to hair swatches.
Example 4: The component activator gel and the all-in-one developer gel were applied to hair swatches.
Example 5: The component activator gel and the component developer gel were applied to hair swatches.

The gels (component or all-in-one) were applied to the hair swatches at room temperature in the following manner:
(A) The activator gel was applied for 90 minutes and then washed off with water; and then
(B) The developer gel was applied for 60 minutes and then washed off with water.

The results are tabulated hereinbelow in table 1 from which it is seen that the combination of the component activator gel and the component developer gel gave the best results.

TABLE 1

Component versus all-in-one gels (hair colour scale values).

| Example | 1 | 2 | 3 | 4 | 5 |
| --- | --- | --- | --- | --- | --- |
| Hair colour scale value | 1.0 | 1.0 | 5.5 | 6.5 | 8.0 |

Example 6

Example 5 was repeated but using the following application method to the hair swatches
(A) The activator gel was applied for 60 minutes and then washed off with water; and then
(B) The developer gelwais applied for 60 minutes and then washed off with water.

The application temperature for each of steps (A) and (B) were varied between room temperature, and 35, 45 and 60 degrees centigrade. The results are tabulated hereinbelow in table 2 from which it is seen that the best results are seen when both steps (A) and (B) are carried out at room temperature.

TABLE 2

The effects of varying the application temperature on the hair colour scale value.

| | Component developer gel at room temperature | Component developer gel at 35 degrees centigrade | Component developer gel at 45 degrees centigrade |
| --- | --- | --- | --- |
| Component activator gel at room temperature | 8.0 | 8.0 | 7.5 |
| Component activator gel at 35 degrees centigrade | 6.5 | 6.5 | 6.5 |
| Component activator gel at 45 degrees centigrade | 5.5 | 5.5 | 5.5 |
| Component activator gel at 60 degrees centigrade | 4.5 | 4.5 | 5.0 |

Examples 7 and 8

Example 5 and example 4 were repeated substituting *Terminalia chebula* extract with epigallocatechin gallate to give examples 7 and 8 respectively. The results for examples 7 and 8 were, using the hair colour scale value, respectively 7 and 5. Thus this result validates the results from examples 1 to 5 hereinabove.

Examples 9 to 15

These examples followed the method set forth for example 6 wherein the activator gel was component A of the component activator gel and the developer gel consisted of a 1:2 weight ratio of component C of the component developer gel and a 2% w/w aqueous solution of polyphenol. The pH of the developer gel was adjusted to 3.5 using hydrochloric acid. The results are tabulated hereinbelow in table 3 from which it is seen that the results vary with the type of polyphenol.

TABLE 3

The effects of varying the polyphenol on the hair colour scale value.

| Example | Polyphenol | Hair colour scale value |
| --- | --- | --- |
| 9 | Catechin | 3.0 |
| 10 | Epigallocatechin | 8.5 |
| 11 | Epigallocatechin gallate | 7.0 |
| 12 | Sunphenon 40R | 6.0 |
| 13 | Sunphenon 90M | 8.0 |
| 14 | Sunphenon 90LB | 9.0 |
| 15 | Methyl gallate | 10.0 |

Examples 16 to 19

These examples followed the method set forth for example 6 wherein the activator gel was component A of the component activator gel and the developer gel consisted of a black tea solution (example 16) or a 3:1 weight ratio of black tea solution and component C of the component developer gel (example 17) or a 2% w/w aqueous solution of Sunphenon 90LB (example 18) or a 2% w/w aqueous solution of Sunphenon 90M (example 19). The results are tabulated hereinbelow in table 4 from which it is seen that substituting *Terminalia chebula* with black tea leads to higher levels of colour in accordance with the hair colour scale value. The black tea solution was prepared by infusing three bags of Lipton Breakfast Tea in 200 ml of boiling water and then boiling the infusion for a further 20 minutes.

TABLE 4

The effects of substituting *Terminalia chebula* with black tea on the hair colour scale value.

| Example | Polyphenol | Hair colour scale value |
| --- | --- | --- |
| 16 | Black tea only | 4.0 |
| 17 | Black tea + *Terminalia chebula* | 5.0 |
| 18 | Black tea + Sunphenon 90LB | 6.0 |
| 19 | Black tea + Sunphenon 90M | 6.0 |

Example 20

This example repeats example 14 but wherein the developer gel is modified by the inclusion of caffeine at a concentration of 0.28% by total weight by addition of a 2% by weight aqueous solution of caffeine to the unmodified developer gel. The result using the hair colour scale value was 7.5 thus good colouring was observed in the presence of caffeine.

Examples 21 to 24

These examples followed the method set forth for example 6 wherein the activator gel was either the component activator gel with component A being a 3.76% w/w aqueous solution of $FeCl_2.4H_2O$ and component C having only 1.12 g propionic acid and 1.68 g KOH (modified component activator gel formulation; pH 5) or the all-in-one activator gel, and the developer gel was either the all-in-one developer gel (which has a pH of 7-8) or the developer gel of example 15 (which has a pH of 3.5), thus:

Example 21: Combination of the modified component activator gel and the all-in-one developer gel;

Example 22: Combination of the modified component activator gel and the developer gel of example 15;

Example 23: Combination of the all-in-one activator gel and the all-in-one developer gel; and Example 24: Combination of the all-in-one activator gel and the developer gel of example 15.

The hair colour scale values are tabulated hereinbelow in table 5 from which it is seen that the best colour levels, in accordance with the hair colour scale value, are observed when the modified component activator gel is combined with the developer gel of example 15. Example 22 suggests that superior colouring is observed when the developer gel has an acidic pH.

TABLE 5

The effects of all-in-one formulations and pH (hair colour scale values).

|  | Modified component activator gel formulation | All-in-one activator gel formulation |
| --- | --- | --- |
| All-in-one developer gel formulation | 5.0 | 5.0 |
| Developer gel of example 15 | 8.5 | 6.0 |

Examples 25 to 28

These examples repeat examples 21 to 24 substituting methyl gallate with Sunphenon 90LB, thus Example 25: Combination of the modified component activator gel (see example 21 hereinabove) and the all-in-one developer gel (modified with Sunphenon 90LB);

Example 26: Combination of the modified component activator gel and the developer gel of example 14;

Example 27: Combination of the all-in-one activator gel and the all-in-one developer gel (modified with Sunphenon 90LB); and Example 28: Combination of the all-in-one activator gel and the developer gel of example 14.

The hair colour scale values are tabulated hereinbelow in table 6 from which it is seen that the results replicate those of examples 21 to 24 insofar as the best colour levels, in accordance with the hair colour scale value, are observed when the modified component activator gel formulation is combined with the developer gel of example 14. Thus Example 26 suggests that superior colouring is observed when the developer gel has an acidic pH (pH (all-in-one developer gel formulation (modified with Sunphenon 90LB)) 7-8; pH (developer gel of example 14) 3.5).

TABLE 6

The effects of all-in-one formulations and pH (hair colour scale values).

| | Modified component activator gel | All-in-one activator gel |
|---|---|---|
| All-in-one developer gel (modified with Sunphenon 90LB) | 5.0 | 5.0 |
| Developer gel of example 14 | 9.0 | 6.0 |

Example 29

Comparative

This example follows the method set forth in example 6 wherein the activator gel was the modified component activator gel disclosed in example 21 hereinabove and the developer gel was component C of the component developer gel adjusted to pH 3.5 with hydrochloric acid. The result using the hair colour scale value was 5.0 thus good colouring was not observed in the absence of another polyphenol.

The invention claimed is:

1. A permanent dye for coloring keratinous fibers comprising:
   (a) A solution of iron (II) or iron (III) salt;
   (b) A solution of an aqueous extract of *Terminalia chebula* and
   (c) A solution of at least one color developer selected from the group consisting of a polyphenol and polyphenol derivatives and mixtures thereof, wherein the solution of the iron (II) or iron (III) salt reacts with the solution of the color developer to form a complex and wherein the solution of polyphenol and polyphenol derivatives is not in the form of an aqueous extract of *Termnalia chebula*.

2. A permanent dye according to claim 1 wherein the polyphenol is selected from the group consisting of epigallocatechin; epigallocatechin gallate; methyl gallate; gallic acid; and an aqueous extract of green tea comprising more than 80% by weight polyphenols, more than 80% by weight catechins and less than 1% by weight caffeine; and mixtures thereof.

3. A permanent dye according to claim 1 wherein the pH of solutions (a) and (b) is in the range 1 to 7.

4. A permanent dye according to claim 1 wherein the iron salt is an iron (II) salt.

5. A method of colouring keratinous fibres using the permanent dye of claim 1, the method comprising the steps of:
   (a) Mixing solutions (b) and (c) thereby to produce solution (d);
   (b) Applying solution (a) to hair; and
   (c) Applying solution (d) to hair,
   wherein steps (a) and (b) may be carried out in either order.

6. A method of colouring keratinous fibres according to claim 5 wherein step (b) precedes step (c).

7. A method of colouring keratinous fibres according to claim 6 wherein the method comprises the additional step of rinsing the hair with water between steps (b) and (c).

8. A method of colouring keratinous fibres according claim 6 wherein one or both of step (b) or step (c) is carried out at room temperature.

9. A dye according to claim 3 wherein the pH of solutions (a) and (b) is in the range of 3 to 7.

10. A dye according to claim 9 wherein the pH of solutions (a) and (b) is in the range of 6 to 7.

* * * * *